(12) United States Patent
Stokowski et al.

(10) Patent No.: US 6,844,927 B2
(45) Date of Patent: Jan. 18, 2005

(54) APPARATUS AND METHODS FOR REMOVING OPTICAL ABBERATIONS DURING AN OPTICAL INSPECTION

(75) Inventors: Stan Stokowski, Danville, CA (US); Zain K. Saidin, San Mateo, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 46 days.

(21) Appl. No.: 10/346,436

(22) Filed: Jan. 15, 2003

(65) Prior Publication Data

US 2004/0100629 A1 May 27, 2004

Related U.S. Application Data

(60) Provisional application No. 60/429,898, filed on Nov. 27, 2002.

(51) Int. Cl.[7] .............................. G01N 21/00
(52) U.S. Cl. ................................. 356/237.1
(58) Field of Search ................ 356/237.1–237.6, 356/601; 219/121.73, 121.83; 359/385, 368, 371, 386

(56) References Cited

U.S. PATENT DOCUMENTS

| | | | | |
|---|---|---|---|---|
| 5,617,203 A | | 4/1997 | Kobayashi et al. ......... | 356/237 |
| 5,805,278 A | * | 9/1998 | Danko ..................... | 356/237.1 |
| 6,038,067 A | * | 3/2000 | George ...................... | 359/368 |
| 6,144,489 A | * | 11/2000 | Wilson et al. ............... | 359/385 |
| 6,717,104 B2 | * | 4/2004 | Thompson et al. .... | 219/121.73 |

OTHER PUBLICATIONS

T.A. Brunner, "Impact of Lens Aberrations on Optical Lithography", IBM J. Res. Develop. vol. 41 No. ½ Jan./Mar. 1997.

* cited by examiner

Primary Examiner—Hoa Q. Pham
(74) Attorney, Agent, or Firm—Beyer, Weaver & Thomas, LLP.

(57) ABSTRACT

Disclosed are methods and apparatus for altering the phase and/or amplitude of an optical beam within an inspection system using one or more spatial light modulator(s) (SLMs). In one embodiment, an apparatus for optically inspecting a sample with an optical beam is disclosed. The apparatus includes a beam generator for directing an incident optical beam onto the sample whereby at least a first portion of the incident optical beam is directed from the sample as an output beam and a detector positioned to receive at least a portion of the output beam. The detector is also operable to generate an output signal based on the output beam. The apparatus further includes one or more imaging optics for directing the output beam to the detector and a programmable spatial light modulator (SLM) positioned within an optical path of the incident or output beam. The SLM is configurable to adjust a phase and/or amplitude profile of the incident beam or the output beam. The apparatus also has a control system operable to configure the SLM to alter the phase and/or amplitude profile of the incident beam or the output beam. For example, the SLM may be configured to alter the illumination profile of the incident beam to achieve different inspection modes. In another example, the SLM may be configured to alter the phase and/or amplitude profile of the output beam so as to substantially eliminate aberrations produced by the imaging optics. In other embodiments, the apparatus may include two or more SLM's which are configurable to alter the phase and/or amplitude profile of both the incident beam and the output beam.

33 Claims, 7 Drawing Sheets

APPARATUS AND METHODS FOR REMOVING OPTICAL ABBERATIONS DURING AN OPTICAL INSPECTION

CROSS REFERENCE TO RELATED APPLICATIONS

This application claims priority of U.S. Provisional Patent Application No. 60/429,898, filed 27 Nov. 2002, which application is incorporated herein by reference in its entirety for all purposes.

BACKGROUND OF THE INVENTION

The present invention relates generally to reticle and integrated circuit design and fabrication systems. More specifically, the invention relates to mechanisms for inspecting reticles and integrated circuits.

Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout typically includes a representational layer for each physical layer of the IC device (e.g., gate oxide, polysilicon, metallization, etc.). Each representational layer is typically composed of a plurality of polygons that define a layer's patterning of the particular IC device.

The reticle writer uses the circuit pattern data to write (e.g., typically, an electron beam writer or laser scanner is used to expose a reticle pattern) multiple reticles that will later be used to fabricate the particular IC design. A reticle or photomask is an optical element containing transparent and opaque, semi-transparent, and phase shifting regions which together define, the pattern of coplanar features in an electronic device such as an integrated circuit. In general terms, reticles are used during photolithography to define specified regions of a semiconductor wafer for etching, ion implantation, or other fabrication processes. For many modern integrated circuit designs, an optical reticle's features are between about 1 and about 5 times larger than the corresponding features on the wafer. For other exposure systems (e.g., x-ray, e-beam, and extreme ultraviolet) a similar range of reduction ratios also apply.

Optical reticles are typically made from a transparent medium such as a borosilicate glass or quartz plate on which is deposited on an opaque and/or semi-opaque layer of chromium or other suitable material. However, other mask technologies are employed for direct e-beam exposure (e.g., stencil masks), x-ray exposure (e.g., absorber masks), etc. The reticle pattern may be created by a laser or an e-beam direct write technique, for example, both of which are widely used in the art.

After fabrication of each reticle or group of reticles, each reticle is typically inspected by illuminating it with light emanating from a controlled illuminator. An optical image of the reticle is constructed based on the portion of the light reflected, transmitted, or otherwise directed to a light sensor. Such inspection techniques and apparatus are well known in the art and are embodied in various commercial products such as many of those available from KLA-Tencor Corporation of San Jose, Calif.

During a conventional inspection process, a target image of a test structure on the reticle is typically compared to a reference image. The reference image is either generated from the circuit pattern data or from an adjacent die on the reticle itself. Either way, the target image features are analyzed and compared with corresponding features of the reference image. Each feature difference is then compared against a threshold value. If the target image feature varies from the reference feature by more than the predetermined threshold, a defect is defined. Similar techniques may be utilized to inspect an integrated circuit (IC).

Unfortunately, these inspection mechanisms frequently result in false defects when the target images significantly differ from their corresponding reference images and these differences are not caused by "real" defects. Several different effects may contribute to the target images differing from the reference images. When the target structures are fabricated from a set of original design patterns which are also used as the reference images, the fabrication process itself introduces discrepancies between the target structures and the reference images. By way of examples, the target structures may become tapered and reduced in size. Target structure corners may also become rounded and/or warped, while edges may become roughened. Imaging of the target structures during inspection also introduces discrepancies between the reference and target images. The imaging process may result in edge enhancement or suppression and contrast changes between the substrate and material, as compared with the design patterns (or reference images). Edges may also appear thickened.

One technique for reducing the number of false defects includes altering the reference image to simulate imaging and/or processing effects until the reference image begins to look like the target image. Several parameters (e.g., corner rounding) of the reference image are typically changed in an iterative process until the reference image resembles the target image. This iterative process is typically complex and time consuming. Although this iterative process may result in a reference image that resembles the target image, it may also unintentionally add a feature to the reference image that corresponds to a "real" defect in the target image so that capture of "real" defects on the target image is hindered. Since a defect is defined as a difference between the reference image and the target image and the reference image has been altered to resemble the target image, this technique may cause "real" defects on the target to be cancelled by simulated portions of the reference image so that the "real" defect are not found.

Accordingly, there is a need for improved mechanisms for inspecting reticles and integrated circuits so that real defects may be reliable found. Additionally, there is a need for reduction in the discrepancies between the reference and corresponding target images caused by imaging effects resulting from imaging of the corresponding test structures.

SUMMARY OF THE INVENTION

Accordingly, the present invention provides mechanisms for altering the phase and/or amplitude of an optical beam within an inspection system using one or more spatial light modulator(s) (SLMs). In one embodiment, an apparatus for optically inspecting a sample with an optical beam is disclosed. The apparatus includes a beam generator for directing an incident optical beam onto the sample whereby at least a first portion of the incident optical beam is directed from the sample as an output beam and a detector positioned to receive at least a portion of the output beam. The detector is also operable to generate an output signal based on the output beam. The apparatus further includes one or more imaging optics for directing the output beam to the detector and a programmable spatial light modulator (SLM) positioned within an optical path of the incident or output beam. The SLM is configurable to adjust a phase and/or amplitude profile of the incident beam or the output beam. The apparatus also has a control system operable to configure the SLM to alter the phase and/or amplitude profile of the incident beam or the output beam. For example, the SLM may be configured to alter the illumination profile of the incident beam to achieve different inspection modes. In another example, the SLM may be configured to alter the phase and/or amplitude profile of the output beam so as to substantially eliminate aberrations produced by the imaging optics. In other embodiments, the apparatus may include two or more SLM's which are configurable to alter the phase and/or amplitude profile of both the incident beam and the output beam.

In a specific implementation, the SLM is positioned within the optical path of the output beam and the adjustment of the phase and/or amplitude profile includes substantially eliminating aberrations from the output beam caused by the imaging optics. In a further aspect, the imaging optics include an objective and the SLM is positioned between the objective and the detector, and the SLM is configurable to alter a phase profile of the output beam. In another specific implementation, the SLM is positioned within the optical path of the incident beam and the adjustment of the phase and/or amplitude profile is performed on the incident beam.

In a further implementation, the SLM includes a plurality of movable mirrors and the control system is operable to adjust a position of one or more of the movable mirrors of the SLM to thereby alter the phase and/or amplitude profile. Adjusting the position of one or more of the movable mirrors may include adjusting a translational position and/or an angle of the one or more of the movable mirrors.

In a specific implementation example, the beam generator includes a light source for generating the incident beam, such as a laser source, and an illumination aperture positioned within the incident beam's optical path. The beam generator also includes a first lens positioned between the laser source and the illumination aperture. The first lens is for directing the incident beam through the illumination aperture. They beam generator also has a field plane aperture positioned after the first lens within the optical path of the incident beam, a relay lens for directing the incident beam through the field plane aperture, and a second lens for imaging the field plane onto the sample. In this example, the SLM may be positioned over the illumination aperture and is configurable to alter the illumination profile of the incident beam. Alternatively, the SLM may be positioned over the field plane aperture and is configurable to alter the illumination profile of the incident beam. In yet another alternative embodiment, the apparatus includes a second SLM (in addition to the first SLM). The first SLM is positioned over the illumination aperture and is configurable to alter the illumination profile of the incident beam, and the second SLM is positioned over the field plane aperture and is also configurable to alter the illumination profile of the incident beam. In a specific implementation, the first and second SLM are each configurable to alter the amplitude profile of the incident beam.

In one aspect, the output beam is reflected from the sample. In another aspect, the output beam is transmitted through the sample. The SLM may be a reflective type SLM or a transmissive type SLM.

In another embodiment, the invention pertains to a method of optically inspecting a sample. An incident optical beam is directed onto the sample whereby at least a first portion of the incident optical beam is directed from the sample as an output beam. The output beam is directed through a first optical path having imaging optics for directing the output beam towards a detector and a programmable spatial light modulator (SLM). The SLM is configured to alter a phase and/or amplitude profile of the output beam so as to substantially eliminate aberrations introduced by the imaging optics.

In a further aspect, the SLM is continually re-configured so that optical aberrations continue to be substantially eliminated. In a specific implementation, configuring the SLM is accomplished by (1) at multiple focal points, optically inspecting a reference pattern having an expected intensity signal or an expected image, where the optical inspection of the reference pattern results in a plurality of measured intensity signals or a plurality of generated images, (2) comparing the measured intensity signals or images obtained from the reference pattern to the expected intensity signal or image, respectively, to obtain a plurality of difference signals or images, (3) the difference signals or images to thereby determine an aberration profile for the imaging optics, and (4) configuring the SLM with a phase and/or amplitude profile that is a reverse of the aberration profile so that the aberration profile is cancelled by the SLM's phase and/or amplitude profile.

In one aspect, the phase and/or amplitude profile of the SLM and the aberration profile of the imaging optics are each a phase map. In another aspect, the incident beam is directed through a second SLM, and the method further includes configuring the second SLM to alter an illumination profile of the incident beam. In a specific application, the illumination profile of the incident beam is altered to occlude a portion of the incident beam from reaching the sample. In a further aspect, the occluded portion is a pupil of the incident beam.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
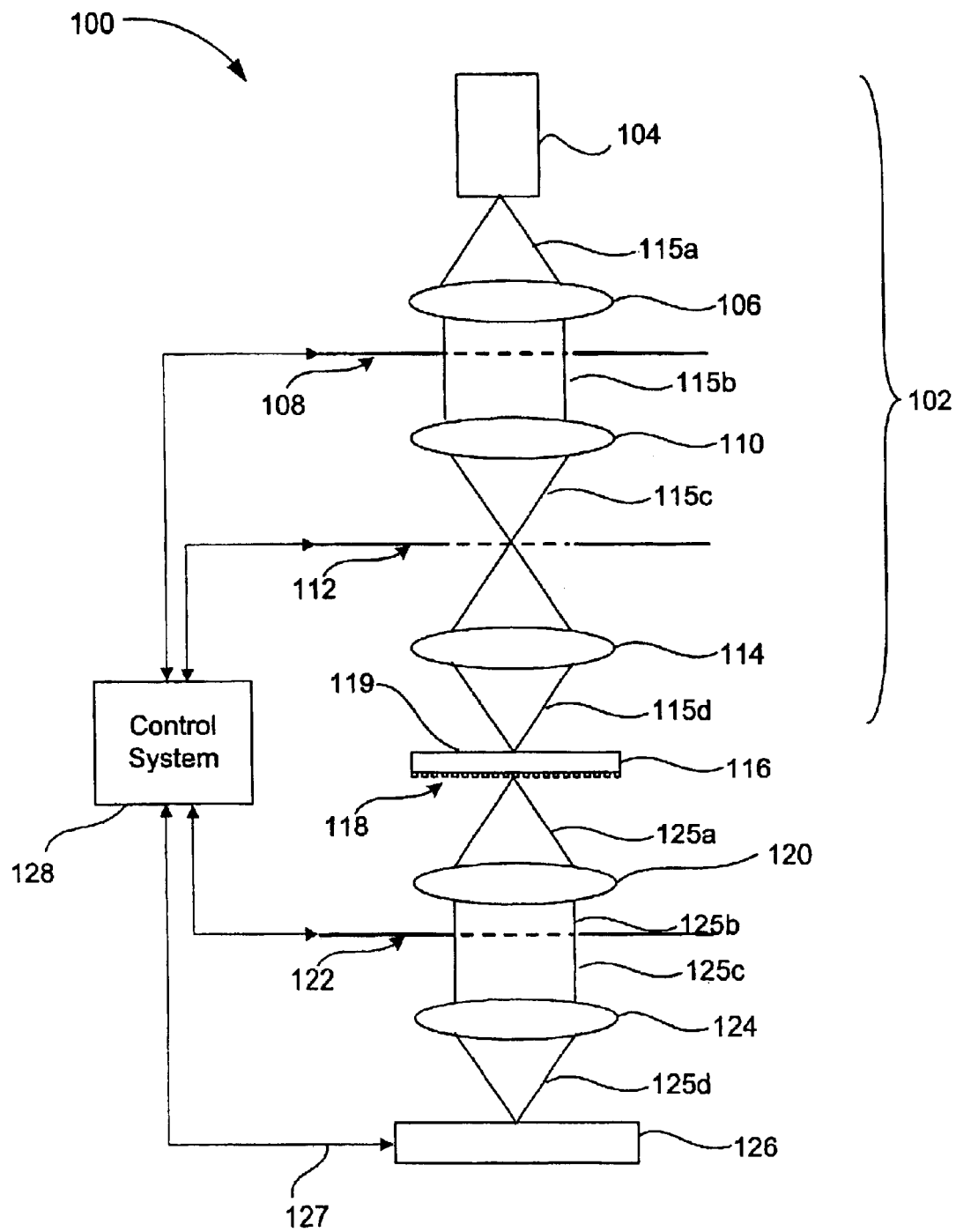
FIG. 1 is a diagrammatic representation of a transmission mode inspection system having transmission type spatial light modulators (SLMs) in accordance with a first embodiment of the present invention.

FIG. 1 is a diagrammatic representation of a transmission mode inspection system 100 having transmission type spatial light modulators (SLMs) in accordance with a first embodiment of the present invention. As shown, the system 100 includes a beam generator 102 for directing an incident optical beam 115 onto sample 116. At least a portion of the incident beam 115 is directed from the sample 116 as an output beam 125 through imaging optics (e.g., 120 and 124) towards detector 126. The detector 126 is generally operable to generate a detected signal 127 that may be transmitted to control system 128 for further processing. Typical features of the control system 128 may include one or more of the following tasks: generating an image of sample 116 based on the detected signal 127, analyzing the detected signal to determine a characteristic (e.g., defect identification) of the sample, and controlling various components of the inspection system 100.

The beam generator 102 may include any suitable light source and optics components for directing the incident beam 115 onto sample 116. In the illustrated embodiment, the beam generator 102 includes laser source 104 for generating a laser beam 115a, lens 106 for receiving the laser beam 115a and outputting collimated beam 115b through illumination aperture 108, a relay lens 110 for receiving collimated beam 115b and focusing such beam through field plane aperture 111, and lens 114 for imaging the field plane 111 as beam 115b onto sample 116. As is readily apparent to those skilled in the art, other optics components may be utilized in addition to or as alternatives to the beam generator optics 102 illustrated in FIG. 1. For example, a critical lens may replace Kohler type lens 106. Rather than collimating beam 115a into collimated beam 115b through illumination aperture 108, the critical lens would serve to focus the beam 115a onto illumination aperture 108. The illumination aperture 108 may then be imaged onto lens 110 in accordance to this alternative embodiment.

The beam generator 102 may also include one or more spatial light modulators (SLM's) for altering the illumination profile of the incident beam 115. However, these SLM's are optional. Each SLM may be configurable to alter the phase and/or amplitude of the incident beam 115 at specific points within the incident beam path. As shown, the inspection system 100 includes a first SLM together with illumination aperture 108 and a second SLM together with field aperture 112. Techniques for utilizing one or both of these SLM's are described further below.

In the illustrated embodiment, at least a portion of the incident beam 115 is transmitted through the sample 116 as output beam 125. As shown, the sample has a thin film pattern on surface 118. However, a pattern may be present on the opposite incident side 119. The sample may take any suitable form which is characterizable with a optical inspection system in a transmission mode (and/or reflection mode as described further below in alternative embodiments with respect to FIGS. 2 and 3). For instance, the sample 116 may be a reticle or photomask, which is later used to fabricate semiconductor devices. By way of other applications, the sample may be a printed circuit board or a silicon wafer or device An output beam 125 is transmitted through the sample 116 as transmitted beam 125a and is received by imaging lens 120. Imaging lens (also referred herein as objective 120) receives transmitted beam 125a, collimates the received 125a, and outputs collimated beam 125b through imaging aperture 122. In the illustrated embodiment, imaging aperture 122 is combined with a spatial light modulator (SLM). This SLM 122 may be configured to adjust the phase and/or amplitude profile of the output beam 125 to substantially eliminate aberrations caused by the imaging optics of system 100. For example, SLM 122 may be configured to eliminate aberrations introduced into the output beam 125 by illumination lens 120. That is, SLM 122 receives collimated output beam 125b and outputs corrected output beam 125c. The corrected output beam 125c is received by lens 124, which focuses such corrected output beam onto detector 126 as detected beam 125d.

The detector 126 may take any suitable form for receiving an optical beam and generating an output signal based on such received optical beam. In one implementation, the detector 126 is a time delay integration (TDI) or a charged coupled device (CDD) type detector. The detector 126 is also preferably coupled to control system 128. The control system may take any form for controlling various components of the inspection system 100 and processing the output signal 127 received from the detector 126. In one implementation, the control system includes a processor and memory which may work together to implement control and signal processing operations.

Generally, the controller techniques described herein may be implemented on software and/or hardware. For example, these techniques can be implemented in an operating system kernel, in a separate user process, in a library package bound into inspection applications, or on a specially constructed machine, such as an optical inspection system available from KLA-Tencor of San Jose, Calif. In a specific embodiment of this invention, some of the techniques of the present invention are implemented in software such as an operating system or in an application running on an operating system. A software or software/hardware hybrid system of this invention may be implemented on a general-purpose programmable machine selectively activated or reconfigured by a computer program stored in memory.

In the illustrated embodiment, the controller is configured to implement various techniques of the present invention. However, the techniques of the present invention may be implemented in any number and type of data processing devices. That is, the techniques of the present invention may be implemented in any suitable combination of hardware and/or software.

Regardless of the controller's configuration, it may employ one or more memories or memory modules configured to store data, program instructions for the general-purpose inspection operations and/or the inventive techniques described herein. The program instructions may control the operation of an operating system and/or one or more applications, for example. The memory or memories may also be configured to store images of target images, reference images, defect classification and position data, as well as values for particular operating parameters of the inspection system.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

Figure 2:
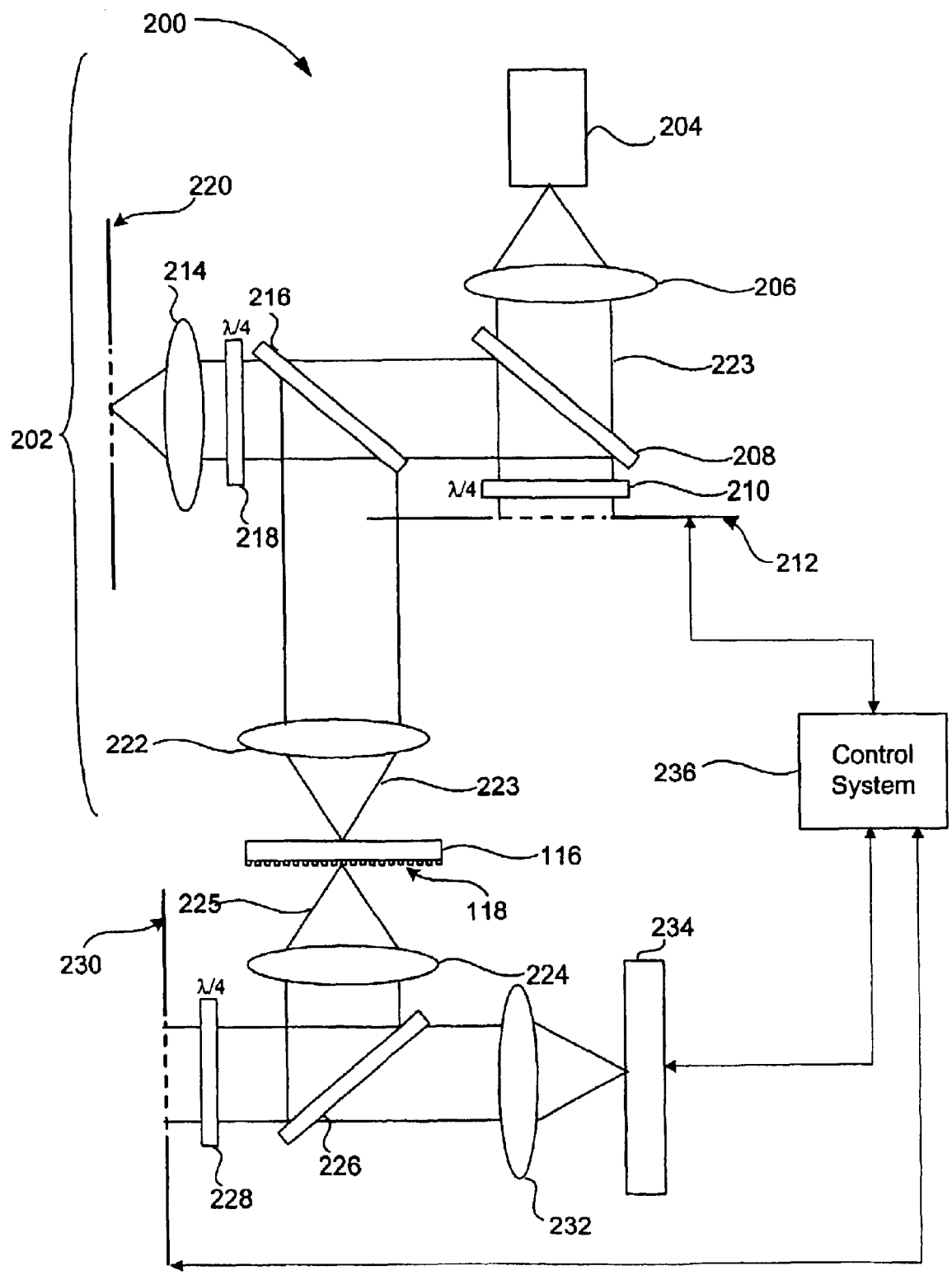
FIG. 2 is a diagrammatic representation of a transmission mode inspection system having reflection type spatial light modulators (SLMs) in accordance with a second embodiment of the present invention.

FIG. 2 is a diagrammatic illustration of a transmission mode system 200 having reflective type SLM's in accordance with a second embodiment of the present invention. Similar to the system of FIG. 1, the system 200 of FIG. 2 includes a beam generator 202 having collimating lens 206, relay lens 214, and focusing lens 222 for directing incident beam 223 onto sample 116 having a pattern on surface 118.

In contrast to the system of FIG. 1, the system 200 of FIG. 2 includes SLM's which are reflective instead of transmissive. Accordingly, the system includes several additional components for reflecting either the incident beam or the output beam off each SLM. As shown, incident beam 223 passes through polar beam splitter (PBS) 208, through one quarter wavelength plate 210 onto reflective SLM 212. The SLM 212 may be configured to alter the illumination profile of the incident beam. The incident beam also reflects off of the SLM 212 and passes through the quarter wavelength plate 210. The quarter wavelength plate 210 alters the polar phase of the incident beam so that PBS 208 reflects the incident beam, instead of transmitting the beam, to PBS 216.

Similarly, the incident beam passes through PBS 216, through quarter wavelength plate 218, and is then focused by lens 214 onto SLM 220. SLM 220 may be configured to alter the illumination profile of the incident beam. The incident beam is then reflected off SLM 220, through lens 214, through quarter wavelength 218, and is reflected off PBF 216 onto lens 222. Lens 222 then focuses the incident beam 223 onto sample 116.

At least a portion of the incident beam 223 is transmitted as output beam 225. The output beam is collimated by imaging lens 224, reflected off PBS 226, and then passes through quarter wavelength plate 228 onto SLM 230. The SLM 230 may be configured to alter the phase and/or amplitude profile of the output beam so as to substantially eliminate aberrations introduced by the imaging optics. The output beam is then reflected off the SLM 230 through quarter wavelength plate 228, through PBF 226, and onto lens 232. Lens 232 then focuses the output beam onto detector 234. The detector and the SLM's are coupled with the control system 236, and the control system 236 and detector may have a similar operation as the control system of FIG. 1.

Figure 3:
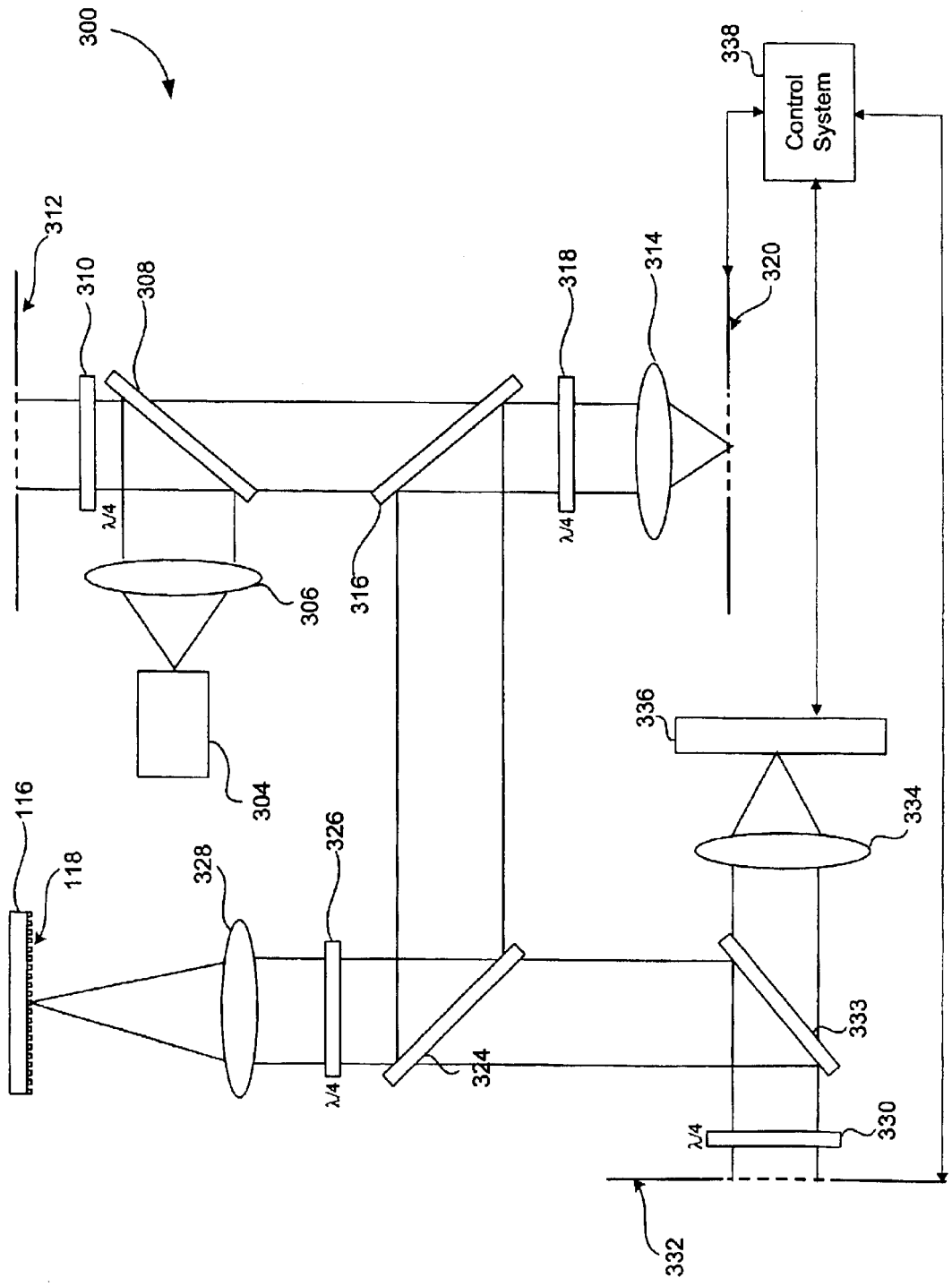
FIG. 3 is a diagrammatic representation of a reflective mode inspection system having reflection type spatial light modulators (SLMs) in accordance with a third embodiment of the present invention.

FIG. 3 is a diagrammatic representation of a reflective mode system 300 having reflective type SLM's in accordance with a third embodiment of the present invention. In an alternative embodiment, the reflective system of FIG. 3 may be combined with the transmission type inspection system of FIG. 1 or 2 into a dual mode inspection system In this illustrated system 300, the incident beam is reflected from sample 116 onto detector 336, instead of being transmitted through such sample as in FIGS. 1 and 2. As illustrated, an incident beam is generated by beam source 304 and directed towards lens 306, which collimates the incident beam. The collimated incident beam is then reflected off PBS 308, through quarter wavelength plate 310, onto reflective SLM 312. The SLM 312 may be configured to adjust the illumination profile of the incident beam and then reflect the incident beam back through quarter wavelength plate 310. The incident beam then passes through PBS 308, through PBS 316 and quarter wavelength plate 318, onto lens 314. Lens 314 focuses the incident beam onto reflective SLM 320.

The SLM 320 may be configured to adjust the illumination profile of the incident beam and then reflect the incident beam back through lens 314 and quarter wavelength plate 318. The incident beam is then reflected off PBS 316 onto PBS 324. The PBS 324 reflects the incident beam through quarter wavelength plate 326 and onto lens 328. Lens 328 then serves to focus the incident beam onto sample 116.

A reflected beam is output from the sample 116 onto lens 328. Lens 328 then collimates the beam through quarter wavelength plate 330 and PBS 324, which outputs the reflected beam onto PBS 333, which reflects the reflected output beam onto SLM 332. The SLM 332 may be configured to alter the phase and/or amplitude profile of the reflected beam such that aberration caused by imaging lens 326 are substantially eliminated.

The reflected beam then passes through quarter wavelength plate 330 and PBS 333 onto lens 334. Lens 334 focuses the reflected beam onto detector 336. The detector and the SLMS are coupled with the control system 338, and the control system 338 and detector of FIG. 3 may have a similar operation as the control system of FIG. 1.

Similar to the system of FIG. 2, this system 300 includes components for directing the incident beam towards each SLM, receiving the resulting incident reflected from such SLM, and directing the incident beam received from each SLM towards the sample 116. As shown, first incident SLM 312 has associated quarter wavelength plate 310 and PBS 308, while second incident SLM 320 has associated quarter wavelength plate 318 and PBS 316. Additionally, imaging SLM 332 has quarter wavelength plate 330 and PBS 328. These components may function similarly to the same named components of FIG. 2.

Any suitable device for altering the phase and/or amplitude profile may be used in place of each SLM. A suitable reflective type SLM is the 0.7 XGA DMD which may be obtained from Texas Instruments of Dallas, Tex. Alternatively, an example transmission type SLM is the HEX-127 available from Meadowlark, Inc. of Frederick, Colo.

Figure 4A:
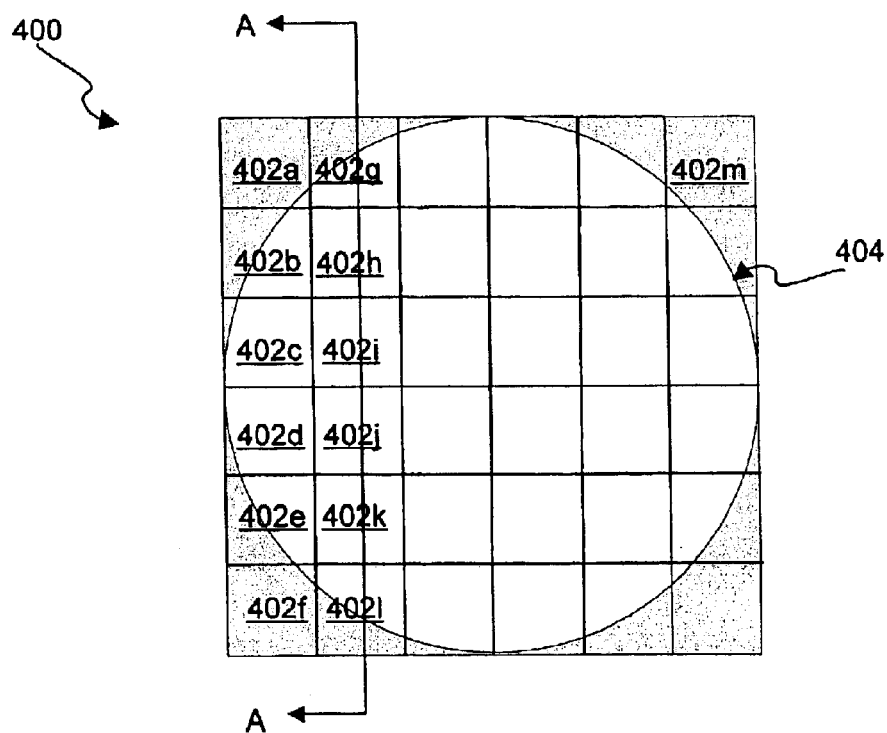
FIG. 4A is a diagrammatic top view of an SLM in accordance with one embodiment of the present invention.

FIG. 4A is a diagrammatic top view of an SLM 400 in accordance with one embodiment of the present invention. As shown the SLM 400 includes a plurality of mirror segments 402. Each mirror segment 402 may be reflective or transmissive. The illustrated SLM 400 also includes aperture 404. Any suitable number of mirror elements 402 may be utilized, and the 6×6 array of the illustrated embodiment is utilized only for illustration purposes.

Figure 4B:
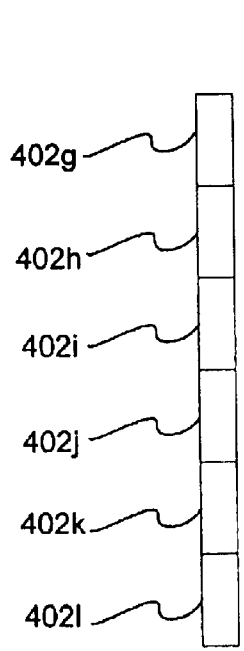
FIG. 4B is a diagrammatic cross sectional view A—A of FIG. 4A, and shows a side view of some of the mirror elements of FIG. 4A at an initial reference position
Figure 4C:
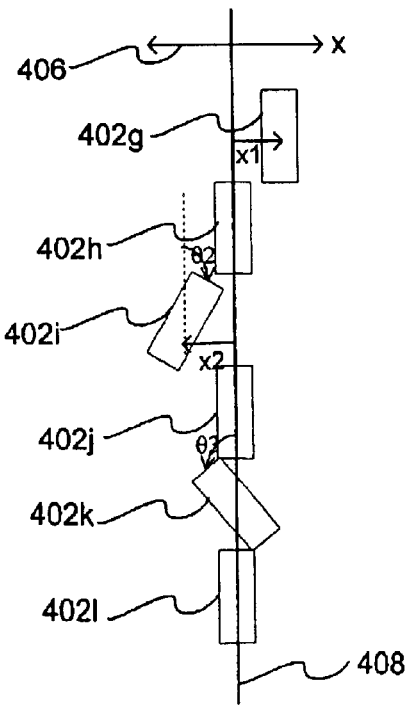
FIG. 4C is a diagrammatic cross sectional view A—A of FIG. 4A, and shows a side view of some of the mirror elements of FIG. 4A at various configured positions.

FIG. 4B is a diagrammatic cross sectional view A—A of FIG. 4A. FIG. 4B shows a side view of mirror elements 402g through 402l. The mirror elements of FIG. 4B are positioned in their initial reference position. However, each mirror element 402 may be configured to change its position as illustrated in FIG. 4C. Referring to FIG. 4C, each mirror element 402 may be moved in direction 406, as well as pivoted. As shown, mirror element 402g has been configured to move distance x1, and mirror element 402i has been configured to move distance −x2. Mirror element 402j has also been configured to rotate through angle θ2. Element 402k has been configured to rotate through angle −θ3.

Figure 5:
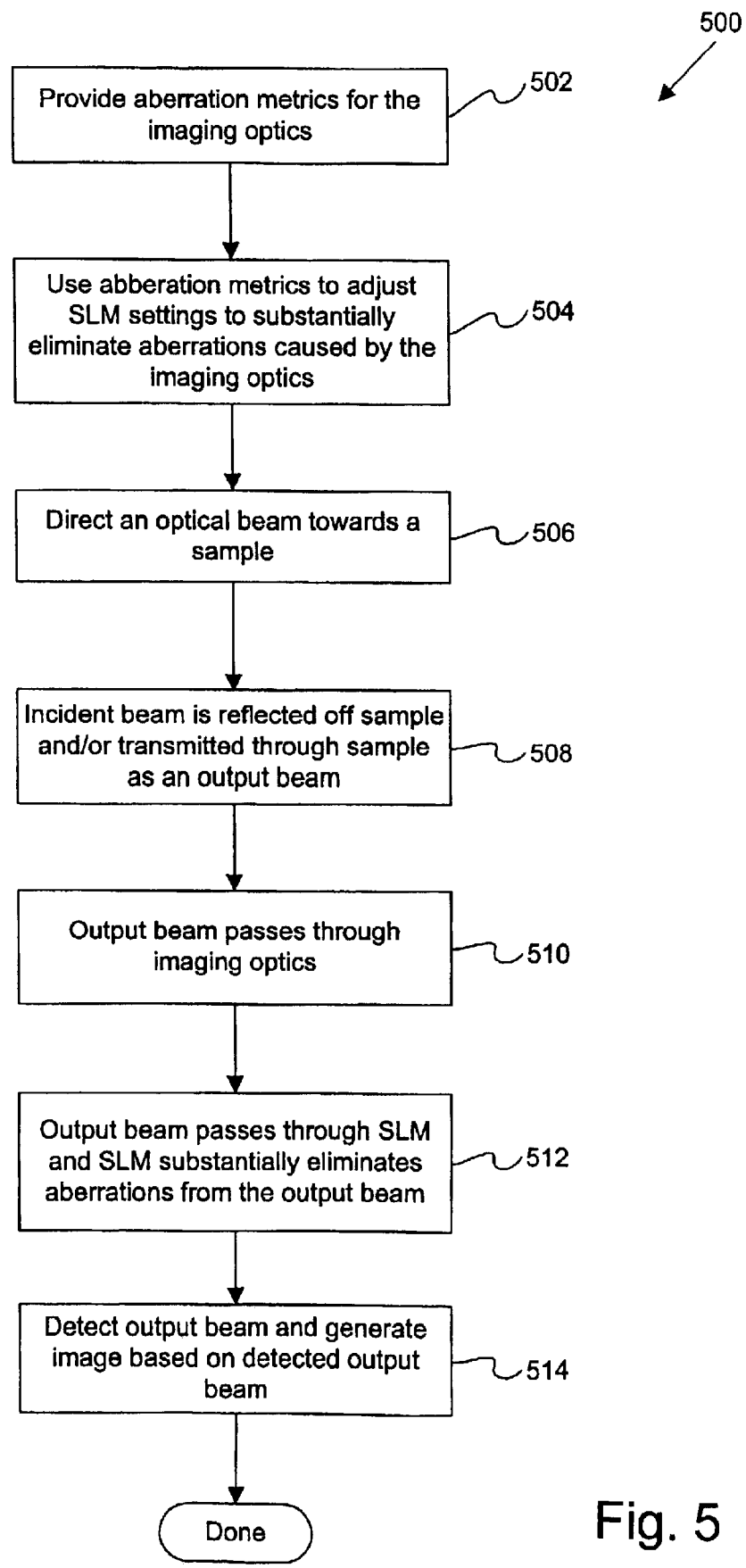
FIG. 5 is a flowchart illustrating a procedure for configuring an SLM to substantially eliminate aberrations of the imaging optics in accordance with one embodiment of the present invention.

Any suitable techniques may be utilized to alter the illumination profile of the incident beam and/or the reflected or transmitted beam of an optical inspection system. FIG. 5 is a flowchart illustrating a procedure for configuring an SLM to substantially eliminate aberrations of the imaging optics in accordance with one embodiment of the present invention. Initially, aberration metrics for the imaging optics are provided in operation 502. The aberration metrics are then be used to adjust one or more SLM settings to thereby substantially eliminate aberrations caused by the imaging optics in operation 504.

The inspection may then commence. In the illustrated embodiment, an optical beam is directed towards a sample in operation 506. The incident beam is then reflected off the sample and/or transmitted through such sample as an output beam in operation 508. The output beam then passes through the imaging optics in operation 510. The output beam then passes through the adjusted SLM, and the SLM substantially eliminates aberrations from the output beam in operation 512. The corrected output beam is then detected and an image may then be generated based on the detected output beam in operation 514. The inspection procedure then ends.

Figure 6:
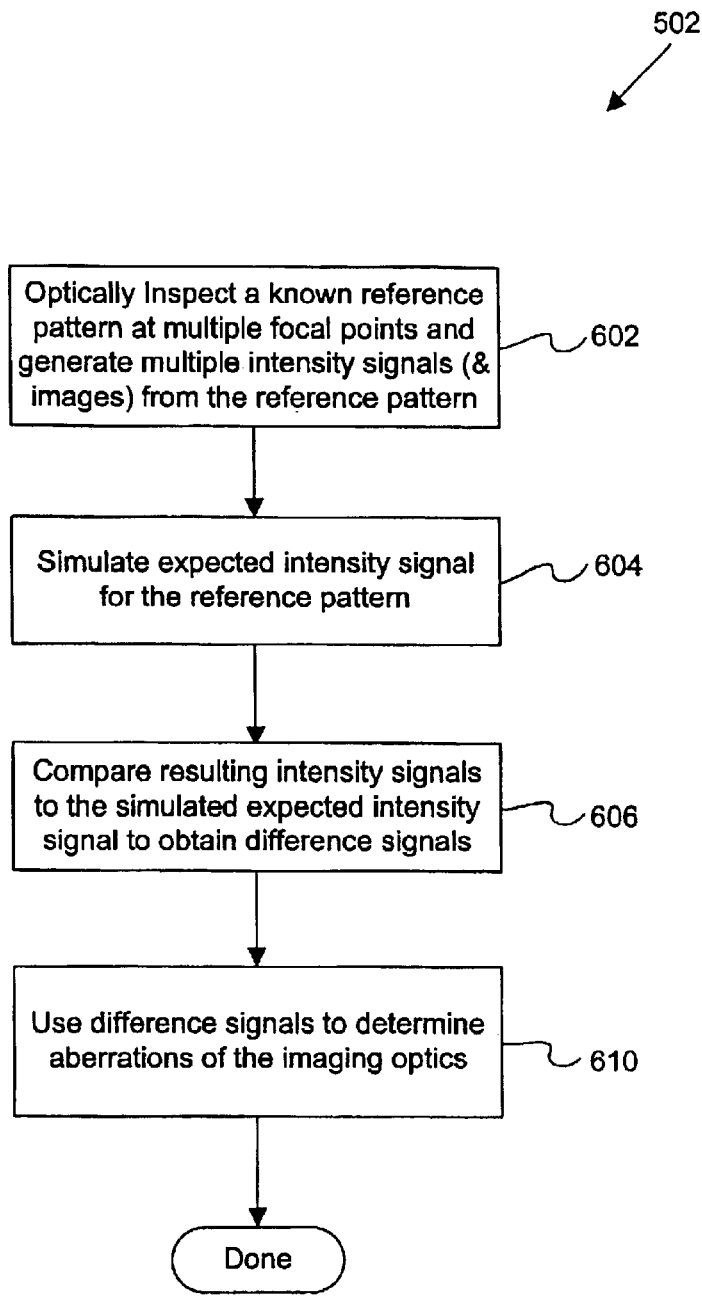
FIG. 6 is flowchart illustrating the operation of FIG. 5 of providing aberration metrics for configuring an SLM to substantially eliminate aberrations caused by the imaging optics in accordance with one embodiment of the present invention.

FIG. 6 is flowchart illustrating the operation 502 of FIG. 5 of providing aberration metrics for configuring of an SLM to substantially eliminate aberrations caused by the imaging optics in accordance with one embodiment of the present invention. Initially, a known reference pattern is optically inspected at multiple focal points, where multiple intensity signals are generated from the reference pattern in operation 602. The multiple intensity signals may also be used to generate multiple images. The expected intensity signal for the reference pattern are then simulated in operation 604. The resulting intensity signals from the reference pattern are then compared to the simulated expected intensity signal to obtain difference signals in operation 606. Alternatively, resulting image signals from the reference pattern may be compared to a simulated expected image in operation 606.

The difference signals (or image differences) are then utilized to determine the aberrations of the imaging optics in operation 610. In general terms, the difference signals are used to identify deviations in the aberrations of the imaging optics. The difference signals or images at multiple focal points provide sufficient information to then calculate the imaging optics aberrations. Generally, these aberrations are expressed in terms of Zernike coefficients, which are orthonormal functions describing the phases variation in the imaging aperture. Techniques for extracting these Zernike coefficients to image differences are well-known to those skilled in the art.

Figure 7:
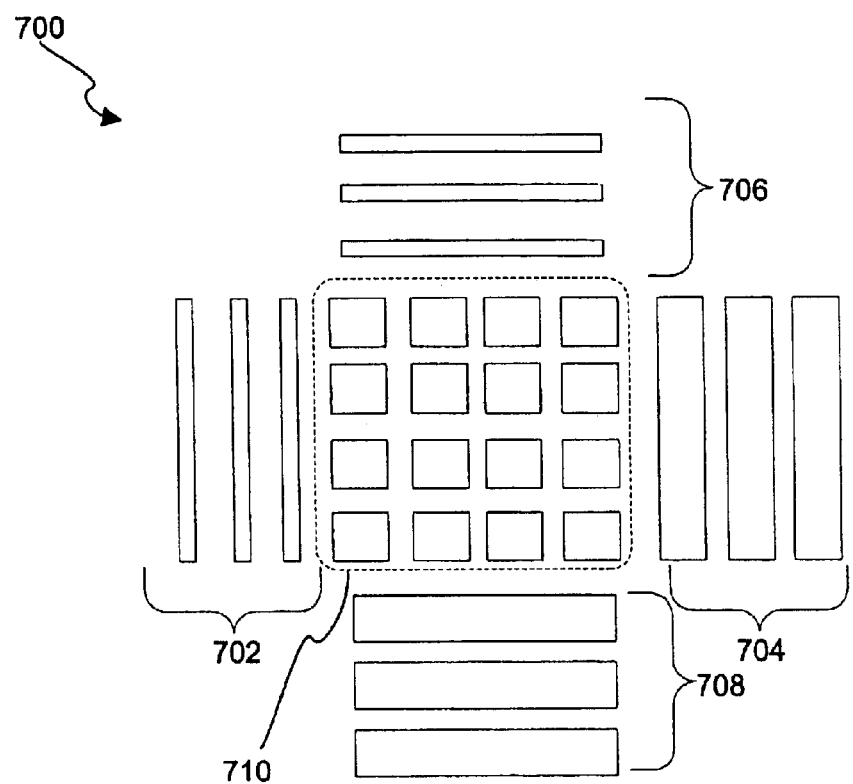
FIG. 7 is a diagrammatic top view of a reference pattern example which may be used to determine aberration metrics.

FIG. 7 is a diagrammatic top view of a reference pattern example which may be used to determine aberration metrics. As shown, the reference pattern 700 includes a set of thin vertical lines 702 and a set of wide vertical lines 704. The reference pattern 700 also includes a set of thin horizontal lines 706 and a set of wide horizontal lines 708. The reference pattern 700 may also include a plurality of contacts 710.

Figures 8A, 8B:
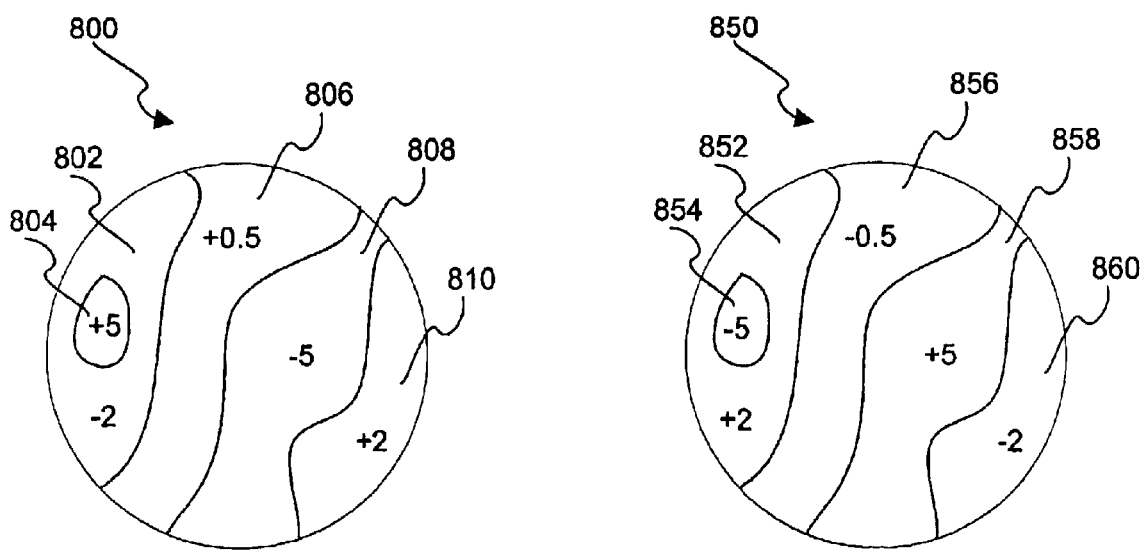
FIG. 8A illustrates a phase contour map for the aberrations across the imaging aperture.
FIG. 8B represents the phase map from a configured SLM which are selected to cancel the aberrations represented in the contour map of FIG. 8A from the imaging optics.

The analysis operation 610 of FIG. 6 may be used to generate a phase contour map for aberrations produced by the imaging optics across the imaging aperture. FIG. 8A illustrates an example phase contour map for the aberrations across the imaging aperture. The phase contour map 800 includes a plurality of areas having different phase shift values. That is, the different areas of the imaging optics will produce different phase shifts. As shown, area 802 has a phase shift of −2 degrees, area 804 has a phase shift of +5, area 806 has a phase shift of +0.5 degrees, area 808 has a phase shift of +−5 degrees, and area 810 has a phase shift of +2 degrees.

This aberration phase contour map may be used to configure the SLM to thereby eliminate these phase shifts aberration within the image field. That is, the mirror elements of the SLM are configured to produce phase shifts which are the reverse of the aberration phase shifts in particular areas of the image field. FIG. 8B represents the results from a configured SLM which operates to cancel the aberrations represented in the contour map of FIG. 8A. That is, the resulting phase contour map of the configured SLM will be a reverse of the phase contour map of the aberrations of FIG. 8A. Accordingly, as shown in FIG. 8B, the contour map 850 of the SLM includes an area 852 having a phase shift +2 degrees which is the reverse of corresponding area 802 of the imaging optics as shown in FIG. 8A. Likewise, SLM contour map 850 contains area 854 having phase shift −5 degrees, area 856 having a phase shift of −0.5 degrees, and area 858 having a phase shift of +5 degrees, and area 858 having a phase shift of +5 degrees and an area 860 having a phase shift of −2 degrees.

Any suitable techniques may also be utilized to configure one or more incident SLMs to alter the illumination profile of the incident beam. A first SLM may be configured to alter the amplitude of various areas of the incident beam field, while a second SLM may be configured to alter the phase of various areas. Alternatively, a single SLM may be utilized to alter both the amplitude and phase of the incident beam's illumination profile. In different inspection modes, it is desirable to occlude a portion of the incident beam. For example, in the phase enhancement inspection mode, one or more SLM's are used to occlude the pupil of the incident beam such that it is smaller than the equivalent pupil of the imaging optics. In another example, in an inspection using a optical arrangement similar to that of lithography systems, one or more SLM's are used to occlude the incident beam to provide a quadrupolar, annular, dipolar, or other type of pupil.

In the incident beam path, one SLM at a pupil or optical Fourier plane may be configured to modify the incident beam angles and a second SLM at a field plane may be configured to modify the illumination areas on the mask. Using two SLMs provides for complete flexibility in determining the incident beam characteristics. For example, at the mask plane an incident beam with a particular amplitude pattern acts as a pattern correlator, which emphasizes certain types of mask patterns.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. An apparatus for optically inspecting a sample with an optical beam, comprising:

a beam generator for directing an incident optical beam onto the sample;

a detector positioned to receive at least a portion of an output beam from the sample, the output beam being in response to the incident beam directed at the sample, the detector being operable to generate an output signal based on the output beam;

imaging optics for directing the output beam to the detector;

a first programmable spatial light modulator (SLM) positioned within an optical path of the output beam and configurable to adjust a phase and amplitude profile of the output beam before the output beam reaches the detector; and a control system operable to configure the first SLM to alter the phase and amplitude profile of the output beam so as to substantially eliminate aberrations from the output beam caused by the imaging optics and to determine a characteristic of the sample based on the detected output signal.

2. An apparatus as recited in claim 1, wherein the control system is operable to determine a characteristic of the sample by being operable to determine whether the sample is defective.

3. An apparatus as recited in claim 2, wherein the imaging optics include an objective and the first SLM is positioned between the objective and the detector.

4. An apparatus as recited in claim 3, wherein the first SLM is positioned after the objective.

5. An apparatus as recited in claim 1, further comprising a second SLM positioned within the optical path of the incident beam, wherein the control system is operable to configure the first SLM to alter the amplitude profile of the incident beam.

6. An apparatus as recited in claim 1, wherein the first SLM includes a plurality of movable mirrors and the control system is operable to adjust a position of each of the movable mirrors of the first SLM to thereby alter the phase and amplitude profile.

7. An apparatus as recited in claim 6, wherein adjusting the position of each movable mirror includes adjusting a translational position and/or an angle of the each movable mirror.

8. An apparatus as recited in claim 1, wherein the apparatus has a reflection inspection mode and at least a portion of the imaging optics form part of the beam generator.

9. An apparatus as recited in claim 1, wherein the control system is further operable to generate an image based on the output signal from the detector and to analyze the generated image to determine the characteristic of the sample.

10. An apparatus as recited in claim 9, wherein the characteristic includes whether the sample has a defect.

11. An apparatus as recited in claim 1, wherein the beam generator comprises:

a light source for generating the incident beam;

an illumination aperture positioned within the incident beam's optical path;

a first lens positioned between the laser source and the illumination aperture, the first lens being for directing the incident beam through the illumination aperture;

a field plane aperture positioned after the first lens within the optical path of the incident beam;

a relay lens for directing the incident beam through field plane aperture; and a second lens for imaging the field plane onto the sample.

12. An apparatus as recited in claim 11, further comprising a second SLM positioned over the illumination aperture and configurable to alter the illumination profile of the incident beam.

13. An apparatus as recited in claim 11, further comprising a second SLM positioned over the field plane aperture and configurable to alter the illumination profile of the incident beam.

14. An apparatus as recited in claim 11, further comprising a second SLM positioned over the field plane aperture for altering the illumination profile of the incident beam and a third SLM positioned over the illumination aperture and configurable to alter the illumination profile of the incident beam.

15. An apparatus as recited in claim 14, wherein the second and third SLM are each operable to alter the amplitude profile of the incident beam.

16. An apparatus as recited in claim 1, wherein the output beam is reflected from the sample.

17. An apparatus as recited in claim 1, wherein the output beam is transmitted through the sample.

18. An apparatus as recited in claim 1, wherein the first SLM is a reflective type SLM.

19. An apparatus as recited in claim 1, wherein the first SLM is a transmissive type SLM.

20. A method of optically inspecting a sample, the method comprising:

directing an incident optical beam onto the sample whereby an output beam is directed from the sample in response to the incident beam, wherein the output beam is directed through a first optical path having imaging optics for directing the output beam towards a detector and a programmable spatial light modulator (SLM);

configuring the SLM to alter a phase and amplitude profile of the output beam so as to substantially eliminate aberrations introduced by the imaging optics prior to the output beam reaching the detector; and determining a characteristic of the sample based on the detected output beam.

21. A method as recited in claim 20, wherein the output beam is transmitted from the sample.

22. A method as recited in claim 20, wherein the output beam is reflected from the sample.

23. A method as recited in claim 20, further comprising continuing to periodically configure the SLM so that optical aberrations continue to be substantially eliminated.

24. A method as recited in claim 20, wherein configuring the SLM is accomplished by:

at multiple focal points, optically inspecting a reference pattern having an expected intensity signal or an expected image, the optical inspection of the reference pattern resulting in a plurality of measured intensity signals or a plurality of generated images;

comparing the measured intensity signals or images obtained from the reference pattern to the expected intensity signal or image, respectively, to obtain a plurality of difference signals or images;

analyzing the difference signals or images to thereby determine an aberration profile for the imaging optics; and configuring the SLM with a phase and amplitude profile that is a reverse of the aberration profile so that the aberration profile is cancelled by the SLM's illumination profile.

25. A method as recited in claim 24, wherein the phase and/or amplitude profile of the SLM and the aberration profile of the imaging optics are each a phase map.

26. A method as recited in claim 20, wherein the incident beam is directed through a second SLM, the method further comprising configuring the second SLM to alter an illumination profile of the incident beam.

27. A method recited in claim 26, wherein the illumination profile of the incident beam is altered to occlude a portion of the incident beam from reaching the sample.

28. A method as recited in claim 27, wherein the occluded portion is a pupil of the incident beam.

29. A method as recited in claim 28, wherein the occluded portion results in particular type of pupil for the incident beam.

30. A method as recited in claim 29, wherein the particular type of pupil is selected from a group consisting of a quadrupolar pupil, an annular pupil, and a dipolar pupil.

31. A method as recited in claim 27, wherein the pupil of the incident beam is occluded such that it is smaller than an equivalent pupil of the imaging optics.

32. A method as recited in claim 26, wherein the incident beam is directed through a third SLM, the method further comprising configuring the third SLM to alter the incident beam's angles of incident, wherein the second SLM is configured to alter illumination areas on the sample.

33. A method as recited in claim 32, wherein the illumination area acts as a pattern correlator and is selected to emphasize particular types of masks.

\* \* \* \* \*